United States Patent [19]

Paparizos et al.

[11] Patent Number: 4,499,308

[45] Date of Patent: Feb. 12, 1985

[54] CATALYTIC REACTION OF ACROLEIN AND METHACROLEIN WITH ALCOHOLS AND GLYCOLS

[75] Inventors: Christos Paparizos, Willowick; Robert S. Shout, Bedford; Wilfrid G. Shaw, Lyndhurst, all of Ohio

[73] Assignee: The Standard Oil Company, Cleveland, Ohio

[21] Appl. No.: 557,777

[22] Filed: Dec. 5, 1983

[51] Int. Cl.³ .............................................. C07C 45/64
[52] U.S. Cl. .................................... 568/465; 568/458; 568/460
[58] Field of Search ..................... 568/465, 458, 460

[56] References Cited

U.S. PATENT DOCUMENTS

| | | | |
|---|---|---|---|
| 2,288,211 | 6/1942 | Schulz | 568/465 |
| 3,259,641 | 7/1966 | Castro | 568/465 |
| 3,795,643 | 3/1974 | Boudiot | 568/465 |

FOREIGN PATENT DOCUMENTS

| | | | |
|---|---|---|---|
| 766489 | 10/1971 | Belgium | 568/465 |
| 1267507 | 9/1959 | France | 568/465 |
| 9411 | 5/1966 | Japan | 568/465 |
| 30046 | 8/1976 | Japan | 568/465 |
| 820095 | 9/1959 | United Kingdom | 568/465 |

*Primary Examiner*—Werren B. Lone
*Attorney, Agent, or Firm*—Charles S. Lynch; John E. Miller, Jr.; Larry W. Evans

[57] ABSTRACT

Disclosed is the reaction acrolein or methacrolein with a mono- or dihydroxyalkane to produce a 3-alkoxypropionaldehyde or a 3-(hydroxyalkoxy)propionaldehyde in the case of acrolein; or to produce a 3-alkoxy-2-methylpropionaldehyde or a 3-(hydroxyalkoxy)-2-methylpropionaldehyde in the case of methacrolein, by contacting a mixture of the recited reactants with a particulate solid metallic catalyst comprising an alloy of palladium and cadmium.

9 Claims, No Drawings

CATALYTIC REACTION OF ACROLEIN AND METHACROLEIN WITH ALCOHOLS AND GLYCOLS

This invention relates to the catalytic reaction of acrolein and methacrolein with mono- or dihydroxyalkanes.

In Chapter 7 in the book, "Acrolein" by C. W. Smith, John Wiley Sons Inc., New York, 1962, it is disclosed that one might produce 3-ethoxypropionaldehyde by the HCl catalyzed addition of ethyl alcohol to acroleins. Similarly, this book reports the reaction of the alcohol and other $C_1$ to $C_4$ alcohols with acrolein in the presence of sodium hydroxide, sulfuric acid or an organic acid-amine salt. See pages 110-113. The best reported result is with respect to the reaction of acrolein with ethanol using a triethylamine-formic acid catalyst; there the conversion of acrolein is 61.5 percent with a selectivity of 94.6 percent. These catalysts must be separated from the desired product.

It is an object of the present invention to provide a catalytic process for etherifying acrolein or methacrolein with lower alcohols or glycols, using a heterogeneous (solid) catalyst easily separable from the reaction mixture.

It is a further object to provide a process for such reaction in the presence of a catalyst capable of providing high yields of the desired product.

Other objects, as well as aspects, features, and advantages, of the invention will be apparent from the disclosure and claims.

These objects are attained according to the invention in which there is provided a method comprising reacting acrolein or methacrolein with a $C_1$ to $C_{12}$, usually $C_1$-$C_5$, monohydroxyalkane or a $C_1$ to $C_5$ dihydroxyalkane to produce a 3-alkoxypropionaldehyde or a 3-(hydroxyalkoxy)propionaldehyde in the case of acrolein; or to produce a 3-alkoxy-2-methylpropionaldehyde or a 3-(hydroxyalkoxy)-2-methylpropionaldehyde in the case of methacrolein, by contacting a mixture of the recited reactants with a particulate solid metallic catalyst comprising an alloy of palladium and cadmium.

The reaction is usually effected in the temperature range of zero to 100° C., or more usually 15°-70° C.

The invention broadly utilizes a Pd—Cd alloy, but an alloy in which the Pd to Cd atomic ratio is 1:0.3 to 1:5 is usual, most often 1:0.5 to 1:2.5.

The molar ratio of the mono- or dihydroxyalkane to aldehyde reactant is at least 1:1 but it is usually at least 5:1 and most usually at least 10:1. There is no particular upper limit, but ratios of more than 50:1 are not needed and therefore entail needless expense.

In the process of the present invention it is easily possible to obtain yields of over 90 percent of the desired product, for instance 3-methoxypropionaldehyde. Moreover, since the catalyst is heterogeneous (a solid) it is very easy to separate from the final product, in contrast to prior art homogeneous catalysts.

The products of the invention are useful as additives to gasoline to improve solubility of small amounts of water. These aldehyde-ethers can also be reduced to the corresponding hydroxy ethers by reaction with sodium and ethyl alcohol. Such products are also useful as gasoline additives for the same purpose as the aldehyde-ethers, as intermediates for surfactants, as chain transfer agents, and as enhanced oil recovery agents.

The following examples are merely illustrative and are not to be considered as limiting.

EXAMPLE 1

In a 200 cc beaker, 0.887 g. of $PdCl_2$ and 2.28 g. of $CdCl_2.2H_2O$ were combined with 10 cc of concentrated (11N) HCl and 65 cc of $H_2O$. Then the mixture was diluted up to 150 cc with Nalco 1034A (40%) silica sol and was stirred moderately with heating to approximately 60° C. The obtained solution was electrolyzed using a Pt wire anode, and a Cu ($\alpha 14$) wire as cathode by applying voltage (2-3v) for 3 hours. The deposit which built up on the cathode was washed off with distilled water and collected periodically. The combined cathode deposits were washed using distilled water and dried in the oven overnight at 110°-120° C. to yield a metallic alloy catalyst in powder form having the empirical formula $PdCd_{2.1}$. Most of the silica did not become part of the catalyst composition.

EXAMPLE 2

A powdered metallic alloy catalyst having the empirical formula $PdCd_{0.5}$ was made exactly as the catalyst of Example 1 was made, except that only 0.57 g. of $CdCl_2$ $2H_2O$ was used instead of 2.28 grams.

EXAMPLE 3

0.15 g. of powdered $PdCd_{2.1}$ prepared as in Example 1 was placed in a 20 cc vial and the vial was sealed. The vial was then flushed with air for 15 minutes using inlet and outlet needles through the septum. Then with a syringe a mixture of 1.34 g. methanol and 0.1 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde was over 93 percent and acrolein conversion was 100 percent.

EXAMPLE 4

0.15 g. of powdered $PdCd_{2.1}$ prepared as in Example 1 was placed in a 20 cc vial and the vial was sealed. The vial was then flushed with oxygen for 15 minutes using inlet and outlet needles through the septum. Then with a syringe a mixture of 1.34 g. methanol and 0.1 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde was 90 percent and acrolein conversion was 98 percent.

EXAMPLE 5

0.15 g. of powdered $PdCd_{2.1}$ prepared as in Example 1 was placed in a 20 cc vial and the vial was sealed. The vial was then flushed with nitrogen for 15 minutes using inlet and outlet needles through the septum. Then with a syringe a mixture of 1.34 g. methanol and 0.1 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde was 90 percent and acrolein conversion was 96 percent.

EXAMPLE 6

0.15 g. of powdered PdCd$_{2.1}$ prepared as in Example 1 was placed in a 20 cc vial and the vial was sealed. The vial was then flushed with air for 15 minutes using inlet and outlet needles through the septum. Then with a syringe a mixture of 1.34 g. methanol and 0.1 g. acrolein was injected, and the reaction mixture stirred, by means of a small magnetic stirrer in the vial, for 16 hours at 21° C. The reaction mixture was analyzed in a Hewlett-Packard Model 5710A gas chromatograph filter with a flame ionization detector and a SP 1200 column. It was found that the yield of 3-methoxypropionaldehyde was 85 percent and acrolein conversion was 90 percent.

EXAMPLE 7

0.075 g. of powdered PdCd$_{2.1}$ prepared as in Example 1 was placed in a 20 cc vial and the vial was sealed. The vial was then flushed with air for 15 minutes using inlet and outlet needles through the septum. Then with a syringe a mixture of 1.34 g. methanol and 0.1 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde was 90 percent and acrolein conversion was 100 percent.

EXAMPLE 8

0.09 g. of powdered PdCd$_{2.1}$ prepared as in Example 1 was placed in a 20 cc vial and the vial was sealed. The vial was then flushed with air for 15 minutes using inlet and outlet needles through the septum. Then with a syringe a mixture of 0.75 g. methanol and 0.19 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde was 50 percent and acrolein conversion was 69.8 percent.

EXAMPLE 9

0.13 g. of powdered PdCd$_{0.5}$ prepared as in Example 2 was placed in a 20 cc vial and the vial was sealed. The vial was then flushed with air for 15 minutes using inlet and outlet needles through the septum. Then with a syringe a mixture of 1.3 g. methanol and 0.09 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde was 95 percent and acrolein conversion was 100 percent.

EXAMPLE 10

0.065 of powdered Pd metal prepared as in Example 2 was placed in a 20 cc vial and the vial was sealed. The vial was then flushed with air for 15 minutes using inlet and outlet needles through the septum. Then with a syringe a mixture of 1.32 g. methanol and 0.09 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of methyl acrylate was 26 percent, but that no 3-methoxypropionaldehyde was formed. Acrolein conversion was 50 percent.

EXAMPLE 11

0.069 g. of powdered Cd metal was placed in a 20 cc vial and the vial was sealed. The vial was then flushed with air for 15 minutes using inlet and outlet needles through the septum. Then with a syringe a mixture of 1.32 g. methanol and 0.09 g. acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. There was no conversion of acrolein.

EXAMPLE 12

0.04 g. of powdered PdCd$_{2.1}$ prepared as in Example 1 was placed in a 20 cc vial and the vial was sealed. The vial was then flushed with oxygen for 15 minutes using inlet and outlet needles through the septum. Then with a syringe a mixture of 0.647 g. of ethylene glycol and 0.023 g. of acrolein was injected, and the reaction mixture stirred, by means of a small magnetic stirrer in the vial, for 16 hours at 50° C. The reaction mixture was analyzed in a Hewlett-Packard Model 5710A g as chromatograph filter with a flame ionization detector and a SP 1200 column. It was found that the main product was 3-(2-hydroxyethoxy)propionaldehyde and that acrolein conversion was 85 percent.

EXAMPLE 13

0.04 g. of powdered PdCd$_{2.1}$ prepared as in Example 1 was placed in a 20 cc vial and the vial was sealed. The vial was then flushed with oxygen for 15 minutes using inlet and outlet needles through the septum. Then with a syringe a mixture of 0.68 g. of n-butanol and 0.02 g. of acrolein was injected, and the reaction mixture stirred, by means of a small magnetic stirrer in the vial, for 16 hours at 50° C. The reaction mixture was analyzed in a Hewlett-Packard Model 5710A g as chromatograph filter with a flame ionization detector and a SP 1200 column. It was found that the main product was 3-n-butoxypropionaldehyde and that acrolein conversion was 82 percent.

EXAMPLE 14

0.15 g. of powdered PdCd$_{2.1}$ prepared as in Example 1 was placed in a 20 cc vial and the vial was sealed. The vial was then flushed with oxygen for 15 minutes using inlet and outlet needles through the septum. Then with a syringe a mixture of 1.5 g. methanol and 0.11 g. of methacrolein was injected, and the reaction mixture stirred, by means of a small magnetic stirrer in the vial, for 16 hours at 50° C. The reaction mixture was analyzed in a Hewlett-Packard Model 5710A g as chromatograph filter with a flame ionization detector and a SP 1200 column. It was found that the main product was 3-methoxyisobutyraldehyde and that methacrolein conversion was 95 percent.

As will be evident to those skilled in the art various modifications of this invention can be made or followed in the light of the foregoing disclosure and discussion without departing from the spirit and scope of the disclosure or from the scope of the claims.

We claim:

1. A method comprising reacting acrolein or methacrolein with a $C_1$ to $C_{12}$ mono- or a $C_1$ to $C_5$ dihydroxyalkane to produce a 3-alkoxypropionaldehyde or a 3-(hydroxyalkoxy)propionaldehyde in the case of acrolein; or to produce a 3-alkoxy-2-methylpropionaldehyde or a 3-(hydroxyalkoxy)-2-methylpropionaldehyde in the case of methacrolein, by contacting a mixture of the recited reactants with a particulate solid metallic catalyst comprising an alloy of palladium and cadmium in the temperature range from zero to 100° C.

2. A method according to claim 1 wherein the molar ratio of the hydroxy compound to the aldehyde reactant is at least 1:1.

3. A method according to claim 1 wherein the molar ratio of the hydroxy compound to the aldehyde reactant is at least 5:1.

4. A method according to claim 1 wherein the molar ratio of the hydroxy compound to the aldehyde reactant is at least 10:1.

5. A method according to claim 1 wherein the hydroxy reactant is methanol.

6. A method according to claim 1 wherein the atomic ratio of Pd to Cd is in the range 1:0.3 to 1:5.

7. A method according to claim 1 wherein the atomic ratio of Pd to Cd is in the range 1:0.5 to 1:2.5.

8. A method according to claim 7 wherein the molar ratio of the hydroxy compound to the aldehyde reactant is at least 1:1.

9. A method according to claim 8 wherein the hydroxy reactant is methanol.

* * * * *